(12) United States Patent
Masuda et al.

(10) Patent No.: US 7,700,709 B2
(45) Date of Patent: Apr. 20, 2010

(54) POLYMERIC DERIVATIVE OF CYTIDINE METABOLIC ANTAGONIST

(75) Inventors: Akira Masuda, Kita-ku (JP); Takeshi Onda, Kita-ku (JP); Hiroko Mashiba, Kita-ku (JP); Keiichirou Yamamoto, Kita-ku (JP); Kazutoshi Takashio, Kita-ku (JP)

(73) Assignee: Nippon Kayaku Kabushiki Kaisha, Tokyo (JP)

(*) Notice: Subject to any disclaimer, the term of this patent is extended or adjusted under 35 U.S.C. 154(b) by 100 days.

(21) Appl. No.: 11/919,912

(22) PCT Filed: Apr. 27, 2006

(86) PCT No.: PCT/JP2006/308826
§ 371 (c)(1),
(2), (4) Date: Nov. 5, 2007

(87) PCT Pub. No.: WO2006/120914
PCT Pub. Date: Nov. 16, 2006

(65) Prior Publication Data
US 2009/0012252 A1    Jan. 8, 2009

(30) Foreign Application Priority Data
May 11, 2005  (JP) .............................. 2005-138249

(51) Int. Cl.
*C08G 61/12* (2006.01)
(52) U.S. Cl. ...................................... 527/201; 528/368
(58) Field of Classification Search .............. 528/368; 527/201
See application file for complete search history.

(56) References Cited

U.S. PATENT DOCUMENTS

| | | | |
|---|---|---|---|
| 5,412,072 A | 5/1995 | Sakurai et al. | 530/322 |
| 6,376,470 B1 | 4/2002 | Greenwald et al. | 514/43 |
| 2002/0183259 A1* | 12/2002 | Choe et al. | 514/19 |

FOREIGN PATENT DOCUMENTS

| | | |
|---|---|---|
| CA | 2 383 240 | 3/2001 |
| EP | 0 397 307 | 3/1990 |
| JP | 2-300133 | 12/1990 |
| JP | 5-955 | 1/1993 |
| JP | 6-206832 | 7/1994 |
| JP | 8-48766 | 2/1996 |
| JP | 2694923 | 9/1997 |
| JP | 2003-524028 | 8/2003 |
| JP | 2004-532289 | 10/2004 |

OTHER PUBLICATIONS

Cancer Research 44, Jan. 25-30, 1984; Yoshinori Kato et al.; "Antitumor Activity of 1-β-D-Arabinofuranosylcytosine Conjugated With Polyglutamic Acid and Its Derivatives".
Journal of Controlled Release 79 (2002) 55-70; Yun H. Choe et al.; "Anticancer drug delivery systems: multi-loaded N4-acyl poly(ethylene glycol) prodrugs of ara-C. II. Efficacy in ascites and solid tumors".

* cited by examiner

*Primary Examiner*—James Seidleck
*Assistant Examiner*—Sonya Wright
(74) *Attorney, Agent, or Firm*—Nields, Lemack & Frame, LLC

(57) ABSTRACT

A derivative of a cytidine metabolic antagonist which can exert a high therapeutic effect at a low dose. A polymeric derivative of a cytidine metabolic antagonist which comprises a polymeric compound having a polyethylene glycol moiety and a polymer moiety having a carboxyl group in a side chain and a cytidine metabolic antagonist, which has such a structure that the carboxyl group in the side chain of the polymeric compound and an amino group in the cytidine metabolic antagonist are bound together to form an amide bond.

10 Claims, 1 Drawing Sheet

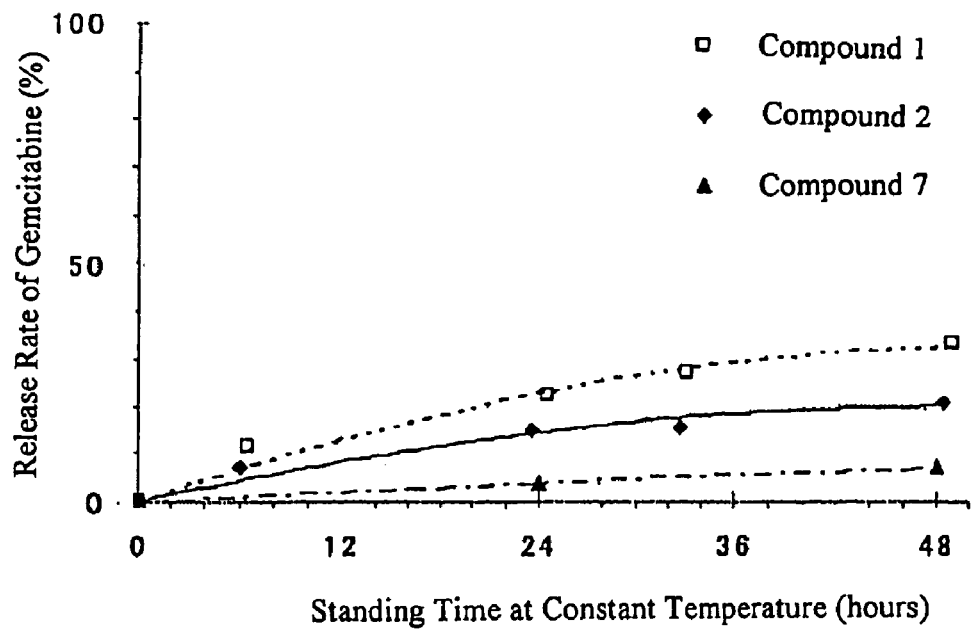
Figure 1: Agent Release in the Absence of Enzyme
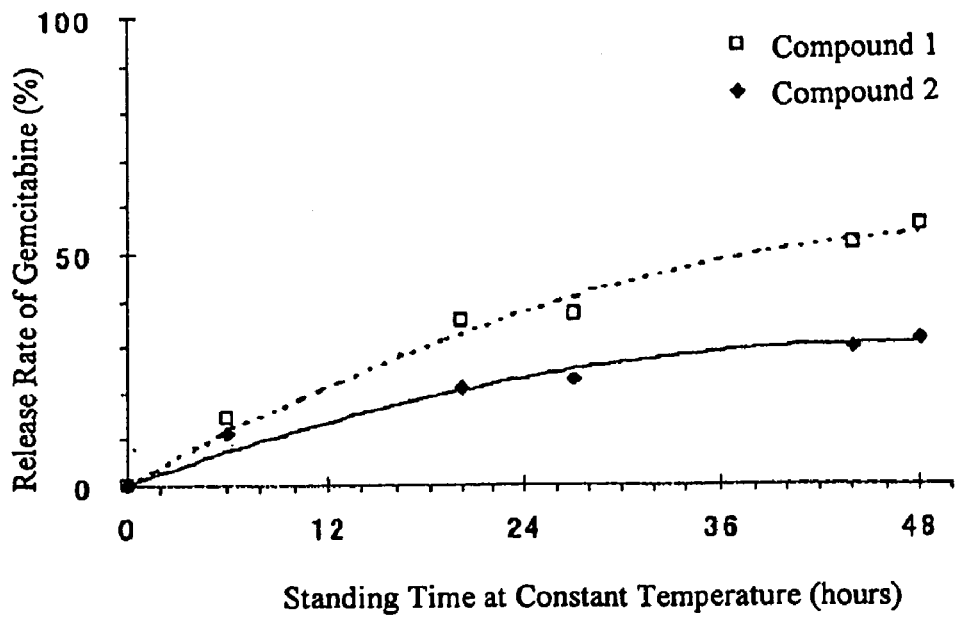
Figure 2: Agent Release in Mouse Plasma

POLYMERIC DERIVATIVE OF CYTIDINE METABOLIC ANTAGONIST

TECHNICAL FIELD

The present invention relates to a polymeric derivative of a cytidine antimetabolite, use thereof, and a method for producing the same.

BACKGROUND ART

Various cytidine antimetabolites have been developed to treat malignant tumors or viral diseases; cytarabine, gemcitabine and the like are clinically used as antitumor (anticancer) agents and zalcitabine, lamivudine and the like as antiviral agents.

However, many of these cytidine antimetabolites cannot sufficiently exert the efficacy thereof themselves or are required to be administered at high doses because they are susceptible to metabolism and excretion in vivo despite exhibiting strong in vitro activities. By way of example, gemcitabine has a strong activity of suppressing cell growth, in vitro, comparable to those of anticancer agents such as paclitaxel and doxorubicin, but needs to be clinically given at a high dose of 1,000 mg/m² body surface area for each administration. This is considered to be due to that the amino group at the 4-position of the base is metabolized and inactivated by cytidine deaminase, a metabolizing enzyme for 2'-deoxycytidine to reduce the in vivo availability thereof (see Non-Patent Document 1).

Binding an agent to a polymer can sometimes improve pharmacokinetics thereof in vivo to enhance the therapeutic effect. Non-Patent Document 2 describes a polymeric derivative in which cytarabine is bound to a polyglutamic acid having an average molecular weight of about 30,000. However, a polymeric derivative of an agent sometimes induces hypersensitive reaction due to immune reaction and, in such a situation, cannot be administered in repeated doses as a agent.

Patent Document 1 describes a polymeric derivative in which a cytidine derivative is bound to a polyethylene glycol, and Non-Patent Document 3 describes a polymeric derivative in which cytarabine is bound to aspartic acid in a polyethylene glycol having the aspartic acid substituted in a branched form at both ends thereof. However, there is also a problem of the possibility that the therapeutic effects of these polymeric derivatives in the clinical are greatly affected by individual difference among patients since the agent release from the derivatives largely depends on hydrolysis reaction by in-vivo enzyme.

Patent Document 2 describes that molecules in each of which an agent is bound to a block-type polymer obtained by condensation of a polyethylene glycol with polyaspartic acid form micelles to provide a medicine. In addition, Patent Document 3 describes a polymer in which an anticancer substance is bound to glutamic acid side chain carboxyl groups of a block-type polymer obtained by condensation of a polyethylene glycol with polyglutamic acid. However, these Patent Documents describe no cytidine antimetabolites as bound agents.

Non-Patent Document 1: Cancer Science, Japanese Cancer Association, Vol. 95, p. 105-111 (2004)
Non-Patent Document 2: Cancer Research, American Association for Cancer Research, Vol. 44, p. 25-30 (1984)
Non-Patent Document 3: Journal of Controlled Release (Elsevier, England), Vol. 79: p. 55-70 (2002)

Patent Document 1: Japanese Patent Application Laying Open (KOHYO) No. Patent Document 2: Japanese Patent No. 2694923
Patent Document 3: Japanese Patent Application Laying Open (KOKAI) No.

DISCLOSURE OF THE INVENTION

Problems to be Solved by the Invention

An object of the present invention is to provide a cytidine antimetabolite having a higher efficacy at a low dose and serving as a new anticancer or antiviral agent.

Means for Solving the Problems

As the result of intensive studies for solving the above problems, the present inventors have found a polymeric derivative of a cytidine antimetabolite, particularly one comprising a structure in which an amino group at the 4-position of a cytidine antimetabolite is amide-bonded to a carboxyl group of a polymeric compound composed of a polyethylene glycol moiety and a polymer moiety having carboxyl groups in the side chains, thereby attaining the present invention.

Specifically, the present invention relates to the following (1) to (13).

(1) A polymeric derivative of a cytidine antimetabolite, comprising a structure in which an amino group of a cytidine antimetabolite is amide-bonded to a carboxyl group in a side chain of a polymeric compound composed of a polyethylene glycol moiety and a polymer moiety having carboxyl groups in the side chains.

(2) The polymeric derivative of a cytidine antimetabolite as described in item (1) above, wherein the polymer moiety having carboxyl groups in the side chains comprises a polyglutamic acid chain.

(3) The polymeric derivative of a cytidine antimetabolite as described in item (1) or (2) above, wherein the derivative is a compound represented by general formula (1):

[Formula 1]

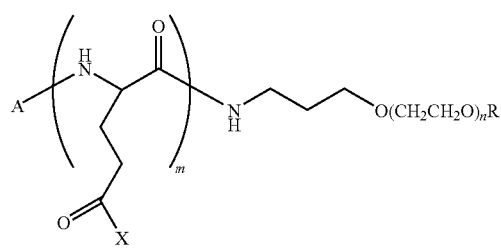

(1)

wherein R represents a hydrogen atom or a C1 to C6 alkyl group; A represents a hydrogen atom, a C1 to C6 acyl group, or a C1 to C6 alkoxycarbonyl group; m represents 3 to 200 as a mean value; n represents 5 to 2,000 as a mean value; X represents a cytidine antimetabolite residue, a hydroxyl group, or a hydrophobic substituent; and X represents a cytidine antimetabolite residue in 3 to 100% of m, a hydroxyl group in 0 to 95% of m and a hydrophobic substituent in 0 to 80% of m.

(4) The polymeric derivative of a cytidine antimetabolite as described in item (3) above, wherein R represents a C1 to C3 alkyl group; A represents a C2 to C4 acyl group; m represents 5 to 100 as a mean value; n represents 50 to 1,000 as a mean value; and the cytidine antimetabolite residue represents a group represented by formula (2):

[Formula 2]

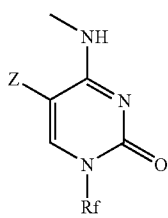

(2)

wherein Z represents a hydrogen atom or a fluorine atom; —Rf represents a group selected from the group consisting of substituents of formula (3):

[Formula 3]

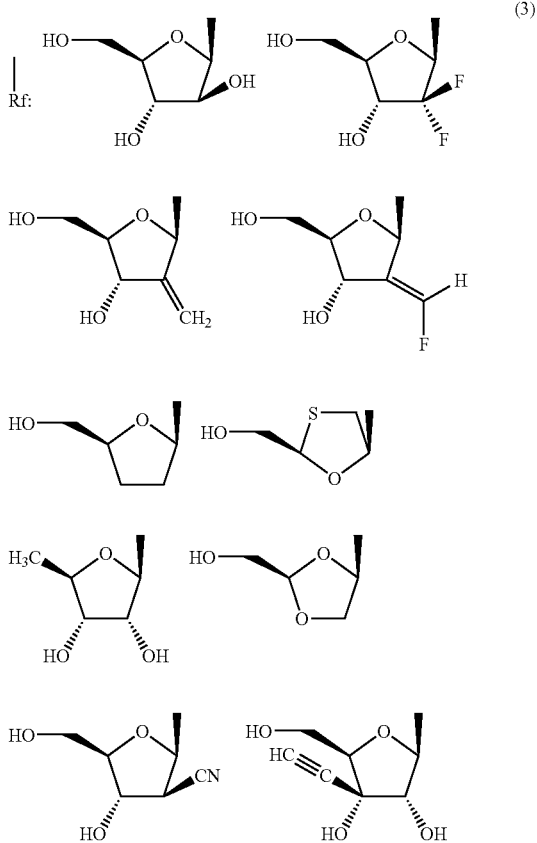

(3)

(5) The polymeric derivative of a cytidine antimetabolite as described in item (3) above, wherein R represents a methyl group; A represents an acetyl group; m represents 10 to 60 as a mean value; n represents 100 to 300 as a mean value; X represents a cytidine antimetabolite residue or a hydroxyl group; and the cytidine antimetabolite represents cytarabine, gemcitabine, or 5'-deoxy-5-fluorocytidine.

(6) The polymeric derivative of a cytidine antimetabolite as described in item (3) or (4) above, wherein the hydrophobic substituent represents an α-amino acid derivative represented by formula (4):

[Formula 4]

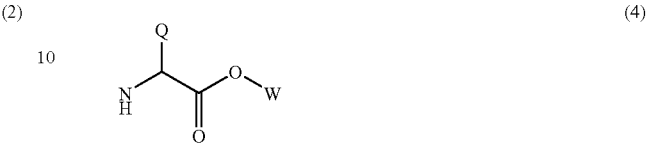

(4)

wherein Q represents a side chain of a neutral amino acid; W represents a C1 to C6 alkyl group or a benzyl group.

(7) The polymeric derivative of a cytidine antimetabolite as described in item (6) above, wherein Q represents an isopropyl group or a benzyl group; and W represents a benzyl group.

(8) The polymeric derivative of a cytidine antimetabolite as described in item (3) or (4) above, wherein the hydrophobic substituent represents a group represented by formula (5):

[Formula 5]

O-T   (5)

wherein T represents a C1 to C6 alkyl group optionally substituted by a phenyl group.

(9) The polymeric derivative of a cytidine antimetabolite as described in item (8) above, wherein T represents a benzyl group, a 3-phenylpropyl group, a 4-phenylbutyl group, or a 5-phenylpentyl group.

(10) The polymeric derivative of a cytidine antimetabolite as described in item (3) above, wherein R represents a methyl group; A represents an acetyl group; m represents 10 to 60 as a mean value; n represents 100 to 300 as a mean value; the cytidine antimetabolite represents cytarabine, gemcitabine, or 5'-deoxy-5-fluorocytidine; and the hydrophobic substituent represents a benzyloxy group, a 4-phenylbutoxy group, a (1-benzyloxycarbonyl-2-methyl)propylamino group, or a (1-benzyloxycarbonyl-2-phenyl)ethylamino group.

(11) An antitumor agent comprising the polymeric derivative of a cytidine antimetabolite as described in any one of items (1) to (10) above as a medicinal ingredient.

(12) An antiviral agent comprising the polymeric derivative of a cytidine antimetabolite as described in any one of items (1) to (10) above as a medicinal ingredient.

(13) A method for producing the polymeric derivative of a cytidine antimetabolite as described in any one of items (1) to (10) above, comprising amide-bonding, using a dehydration condensation agent in an organic solvent, an amino group of a cytidine antimetabolite to a carboxyl group in a side chain of a polymeric compound composed of a polyethylene glycol moiety and a polymer moiety having carboxyl groups in the side chains.

EFFECT OF THE INVENTION

The polymeric derivative of a cytidine antimetabolite according to the present invention has a structure in which an amino group at the 4-position of a cytidine antimetabolite is amide-bonded to a carboxyl group of a polymeric compound composed of a polyethylene glycol moiety and a polymer moiety having carboxyl groups in the side chains. The derivative can slowly release the cytidine antimetabolite in vivo and is useful as an anticancer or antiviral agent having an excellent therapeutic effect at a low dose. In addition, having the property of slowly releasing the agent enzyme-independently makes the derivative one whose therapeutic effect is less affected by individual difference among patients. The polymeric derivative forming micelles selectively accumulates in the affected part and serves as an agent having a higher efficacy with reduced side effects.

BRIEF DESCRIPTION OF THE DRAWINGS

FIG. 1 is a graph showing the time courses of agent release in the absence of enzyme; and FIG. 2 is a graph showing the time courses of agent release in mouse plasma.

BEST MODE FOR CARRYING OUT THE INVENTION

The polymeric derivative of a cytidine antimetabolite according to the present invention comprises a structure in which an amino group of a cytidine antimetabolite is amide-bonded to a carboxyl group in a side chain of a polymeric compound composed of a polyethylene glycol moiety and a polymer moiety having carboxyl groups in the side chains.

For the purpose of the present invention, "cytidine antimetabolite" is not particularly limited provided that it is a 4-aminopyrimidin-2-one derivative while being a compound having an antitumor or antiviral activity, and refers to a compound represented by formula (2) wherein the nucleic acid base moiety is cytosine (where Z is a hydrogen atom) or 5-fluorocytosine (where Z is a fluorine atom); and the group (Rf) bound thereto is a group selected from the group consisting of the substituents of the above formula (3).

Specific examples thereof include cytarabine, gemcitabine, 2'-deoxy-2'-methylidenecytidine (DMDC), tezacitabine, zalcitabine, lamivudine, 5'-deoxy-5-fluorocytidine (5'-DFCR), troxacitabine, 2'-C-cyano-2'-deoxy-1-β-D-arabinofuranosyl cytosine (CNDAC), 3'-ethynylcytidine, and (−)-β-L-dioxolanecytidine.

According to the present invention, examples of the polymer moiety having carboxyl groups in the side chains in the "polymeric compound composed of a polyethylene glycol moiety and a polymer moiety having carboxyl groups in the side chains" include a graft-type polymer in which carboxylic acid chains branch from the polymer backbone or a block-type polymer in which polycarboxylic acid polymers are condensed.

Examples of the polymeric compound in which the polymer moiety having carboxyl groups in the side chains is the graft-type polymer include a polymer obtained, for example, by the copolymerization reaction of a condensate of polyethylene glycol and an acrylic acid with an acrylic acid, maleic anhydride or the like, followed by optional hydrolysis reaction as described in Japanese Patent Application Laying Open (KOKAI) No. 11-279083.

Examples of the polymeric compound in which the polymer moiety having carboxyl groups in the side chains is the block-type polymer include a compound in which a polyethylene glycol having a terminal functional group is bound to a polycarboxylic acid having a functional group at the end, or a compound obtained by the polymerization reaction of an amino acid activated compound in which the polymerization starts with a polyethylene glycol having an amino group at the end as described in Patent Document 3.

Examples of the polymer having carboxyl groups in the side chains include polyacrylic acid, polymethacrylic acid, polymalic acid, and polyglutamic acid; preferred is polyglutamic acid.

For the purpose of the present invention, "polyethylene glycol" may be a polyethylene glycol derivative, both or one end of which is modified, in which case the groups modifying both of the ends may be identical or different. Examples of the terminal modifying group include a C1 to C6 alkyl group optionally having a substituent; preferred is a C1 to C4 alkyl group optionally having a substituent.

Examples of the C1 to C6 alkyl group in the C1 to C6 alkyl group optionally having a substituent include a straight-chain, branched or cyclic C1 to C6 alkyl group. Specific examples thereof include a methyl group, an ethyl group, a propyl group, an isopropyl group, a butyl group, an isobutyl group, a t-butyl group, a pentyl group, an isopentyl group, a 2-methylbutyl group, a neopentyl group, a 1-ethylpropyl group, a hexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, a 2-ethylbutyl group, a cyclopropyl group, a cyclopentyl group, and a cyclohexyl group. Preferred is a C1 to C4 alkyl group; specific examples thereof include a methyl group, an ethyl group, an n-propyl group, an isopropyl group, an n-butyl group, an s-butyl group, and a t-butyl group. Particularly preferred is a methyl group, an ethyl group, an n-propyl group, or an isopropyl group.

The substituent in the C1 to C6 alkyl group optionally having a substituent is not particularly limited; however, examples thereof include an amino group, a methylamino group, a dimethylamino group, an ethylamino group, and a diethylamino group. Preferred is an amino group.

According to the present invention, the polyethylene glycol derivative, both ends of which are modified, is preferable. Specific examples thereof include a polyethylene glycol derivative having a C1 to C6 alkyl group at one end and an amino-C1 to C6 alkyl group at the other end. Preferred is a polyethylene glycol derivative having a C1 to C3 alkyl group at one end and an amino-C1 to C4 alkyl group at the other end. Particularly preferred is a polyethylene glycol derivative having a methyl group at one end and an aminopropyl group at the other end.

According to the present invention, "polyethylene glycol" has a weight average molecular weight of about 200 to 500,000, preferably about 500 to 100,000, more preferably about 2,000 to 50,000.

According to the present invention, the "polymeric compound composed of a polyethylene glycol moiety and a polymer moiety having carboxyl groups in the side chains" is preferably a block-type polymer, more preferably a block copolymer of a polyethylene glycol with a polymer having carboxyl groups in the side chains.

Examples of the block copolymer of a polyethylene glycol with a polymer having carboxyl groups in the side chains include an alkoxypolyethylene glycol-polyacrylic acid, an alkoxypolyethylene glycol-polymethacrylic acid, and an alkoxypolyethylene glycol-polyglutamic acid; preferred is methoxypolyethylene glycol-polyglutamic acid.

According to the present invention, the "polymeric compound composed of a polyethylene glycol moiety and a polymer moiety having carboxyl groups in the side chains" has an average carboxyl group number per molecule of about 3 to 200, preferably about 5 to 100, more preferably about 10 to 60.

According to the present invention, the "polymeric compound composed of a polyethylene glycol moiety and a polymer moiety having carboxyl groups in the side chains" has a weight average molecular weight of about 500 to 500,000, preferably about 2,000 to 100,000, more preferably about 3,000 to 50,000.

According to the present invention, the amount of the cytidine antimetabolite amide-bonded to the polymeric compound composed of a polyethylene glycol moiety and a polymer moiety having carboxyl groups in the side chains is not particularly limited provided that it is within the range from one to the total number of the carboxyl groups for each polymeric compound, and may be that amount which is enough to exert drug effect when the compound is administered in vivo. Preferred is 3 to 100%, more preferably 5 to 70%, of the total carboxyl group number of the polymer.

The above bonding amount can be determined from the intensity of ultraviolet absorption spectrum of a compound of the present invention. The amount can also be determined by subjecting the polymeric derivative of a cytidine antimetabolite according to the present invention to alkaline hydrolysis to quantitate the released cytidine antimetabolite, for example, by high performance liquid chromatography.

A typical compound as the polymeric derivative of a cytidine antimetabolite according to the present invention is a compound represented by the above general formula (1), wherein R represents a hydrogen atom or a C1 to C6 alkyl group; A represents a hydrogen atom, a C1 to C6 acyl group, or a C1 to C6 alkoxycarbonyl group; m represents 3 to 200 as a mean value; n represents 5 to 2,000 as a mean value; X represents a cytidine antimetabolite residue, a hydroxyl group, or a hydrophobic substituent; X represents the cytidine antimetabolite residue in 3 to 100% of m, the hydroxyl group in 0 to 95% of m and the hydrophobic substituent in 0 to 80% of m.

In the formula (1), the C1 to C6 alkyl group for R has the same meaning as the above-described alkyl group; a preferable group is also the same as above.

Examples of the C1 to C6 acyl group for A in the formula (1) include a formyl group, an acetyl group, a propionyl group, a butyryl group, an isobutyryl group, a valeryl group, an isovaleryl group, a pivaloyl group, and a hexanoyl group. Preferred is a C2 to C4 acyl group, for example, an acetyl or propionyl group; more preferred is an acetyl group.

Examples of the C1 to C6 alkoxycarbonyl group for A in the formula (1) include a methoxycarbonyl group, an ethoxycarbonyl group, a propoxycarbonyl group, an isopropoxycarbonyl group, an n-butoxycarbonyl group, a tert-butoxycarbonyl group, a pentoxycarbonyl group, a hexyloxycarbonyl group, a cyclopropoxycarbonyl group, a cyclopentyloxycarbonyl group, and a cyclohexyloxycarbonyl group. Preferred is a methoxycarbonyl group, an ethoxycarbonyl group, a propoxycarbonyl group, an isopropoxycarbonyl group, a butoxycarbonyl group, or a tert-butoxycarbonyl group; more preferred is an ethoxycarbonyl group or a tert-butoxycarbonyl group.

In the formula (1), m is, as a mean value, 3 to 200, preferably 5 to 100, more preferably 10 to 60.

In the formula (1), n is, as a mean value, 5 to 2,000, preferably 50 to 1,000, more preferably 100 to 300.

In the general formula (1) for the polymeric derivative of a cytidine antimetabolite according to the present invention, the glutamic acid derivatives in each of which X is a cytidine antimetabolite residue, a hydroxyl group or a hydrophobic substituent may be bound randomly or by forming blocks.

In the formula (1), the cytidine antimetabolite residue for X means the residue of the above cytidine antimetabolite; particularly preferred examples of the cytidine antimetabolite include cytarabine, gemcitabine, and 5'-deoxy-5-fluorocytidine.

In the formula (1), examples of the hydrophobic substituent for X include various substituents; the substituent is not particularly limited provided that it does not impair the exertion of the drug effect of the polymeric derivative of a cytidine antimetabolite. However, preferred examples thereof include an α-amino acid derivative represented by the above formula (4), wherein Q represents a side chain of a neutral amino acid; W represents a C1 to C6 alkyl group or a benzyl group, and a group represented by the above formula (5), wherein T represents a C1 to C6 alkyl group optionally substituted by a phenyl group.

Examples of the side chain of a neutral amino acid for Q in the formula (4) include residues of natural amino acids, such as a hydrogen atom, a methyl group, an isopropyl group, an isobutyl group, an s-butyl group, a benzyl group, a hydroxymethyl group, a 1-hydroxyethyl group, a carbamoylmethyl group, and a 2-carbamoylethyl group, and derivatives of residues of amino acids, such as a tert-butoxymethyl group, a benzyloxymethyl group, a benzyloxycarbonylmethyl group, and a 2-benzyloxycarbonylethyl group. Preferred examples thereof include an isopropyl group, an isobutyl group, an s-butyl group, a benzyl group, a benzyloxymethyl group, a benzyloxycarbonylmethyl group, and a 2-benzyloxycarbonylethyl group; more preferred is an isopropyl group, a benzyl group, a benzyloxymethyl group, or 2-benzyloxycarbonylethyl group; particularly preferred is an isopropyl group or a benzyl group.

Examples of the C1 to C6 alkyl group for W in the formula (4) include the same group as the above alkyl group; a preferable group is the same as above.

The C1 to C6 alkyl group for T in the formula (5) has the same meaning as the above-described alkyl group; a preferable group is also the same as above. Examples of the group represented by the formula (5) include a methoxy group, an ethoxy group, an n-propoxy group, an isopropoxy group, an n-butoxy group, a tert-butoxy group, an n-pentyloxy group, an n-hexyloxy group, a cyclopropyloxy group, a cyclopentyloxy group, a cyclohexyloxy group, a cyclohexylmethoxy group, a benzyloxy group, a 2-phenethyloxy group, a 3-phenylpropoxy group, a 4-phenylbutoxy group, a 5-phenylpentyloxy group, and a diphenylmethoxy group.

Examples of the hydrophobic substituent also include amino groups such as a methylamino group, an ethylamino group, an n-propylamino group, an isopropylamino group, an n-butylamino group, an isobutylamino group, an n-pentylamino group, an n-hexylamino group, a cyclopropylamino group, a cyclopentylamino group, a cyclohexylamino group, a cyclohexylmethylamino group, a dicyclohexylmethylamino group, an anilino group, a benzylamino group, a 2-phenethylamino group, a 3-phenylpropylamino group, a 4-phenylbutylamino group, and a diphenylmethylamino group.

The hydrophobic substituent for X in the formula (1) is particularly preferably a benzyloxy group, a 3-phenylpropoxy group, a 4-phenylbutoxy group, a 5-phenylpentoxy group, a (1-benzyloxycarbonyl-2-methyl)propylamino group or a (1-benzyloxycarbonyl-2-phenyl)ethylamino group, and more particularly preferably a benzyloxy group, a 4-phenylbutoxy group, a (1-benzyloxycarbonyl-2-methyl)propylamino group or a (1-benzyloxycarbonyl-2-phenyl)ethylamino group.

In the formula (1), the proportion of a cytidine antimetabolite residue for X is 3 to 100%, preferably 5 to 70% based on the total carboxyl group number (m) of the polymer; the proportion of a hydroxyl group for X is 0 to 95%, preferably 5 to 70% based on the m; and the proportion of a hydrophobic substituent for X is 0 to 80%, preferably 20 to 70% based thereon.

In the polymeric derivative of a cytidine antimetabolite according to the present invention, when a side chain carboxyl group to which the cytidine antimetabolite does not bind is present, the carboxyl group may be in a free form or in an alkaline salt form. When obtained in a free form, the carboxyl group can be converted into a desired salt form by a method known per se or a method based thereon. Conversely, when obtained in a salt form, the carboxyl group can be converted into a free form or another desired salt form by a method known per se or a method based thereon.

Examples of the alkaline salt include salts of lithium, sodium, potassium, magnesium, ammonium and triethylammonium.

In the polymeric derivative of a cytidine antimetabolite according to the present invention, the structural units constituting the polymer moiety having carboxyl groups in the side chains may be, when optical isomers are present, optically active substances, a racemate, or a mixture thereof in any proportion. For example, when the polymer moiety having carboxyl groups in the side chains is a polyglutamic acid derivative, the derivative may be a polymer in which poly-L-glutamic acid, poly-D-glutamic acid, and a side chain-substituted L-glutamic acid or a side chain-substituted D-glutamic acid are bound in any order in any proportion.

Particularly preferred examples of the polymeric derivative of a cytidine antimetabolite according to the present invention include compounds shown in Table 1 below.

In Table 1, Bzl indicates a benzyl group; Val, valine; Phe, phenylalanine; and C4H8Ph, a 4-phenylbutyl group. In X, the substitution percentages are approximate values; the rest other than the residue and group described in the table is a hydroxyl group. As cytidine antimetabolites for X, cytarabine, gemcitabine, 5'-deoxy-5-fluorocytidine, 2'-deoxy-2'-methylidenecytidine (DMDC), 3'-ethynylcytidine, 2'-C-cyano-2'-deoxy-1-β-D-arabinofuranosyl cytosine (CNDAC) and (−)-β-L-dioxolanecytidine are the following compounds.

TABLE 1

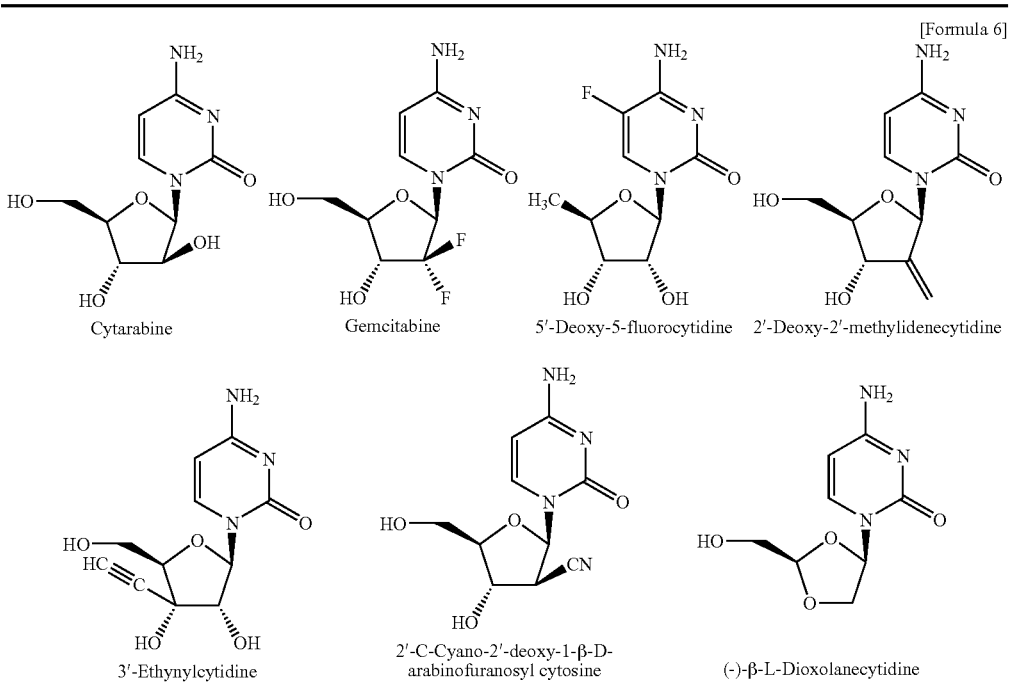

[Formula 6]

| No. | R | n (mean) | m (mean) | A | X: Cytidine Antimetabolite (percentage) | X: Hydrophobic Substituent (percentage) |
|---|---|---|---|---|---|---|
| 1 | CH₃ | 272 | 32 | CH₃CO | Cytarabine (30%) | OBzl (50%) |
| 2 | CH₃ | 272 | 32 | CH₃CO | Cytarabine (30%) | Phe-OBzl (40%) |
| 3 | CH₃ | 272 | 25 | CH₃CO | Cytarabine (20%) | Phe-OBzl (60%) |
| 4 | CH₃ | 272 | 23 | CH₃CO | Gemcitabine (15%) | Phe-OBzl (60%) |
| 5 | CH₃ | 272 | 23 | CH₃CO | Gemcitabine (15%) | Val-OBzl (60%) |
| 6 | CH₃ | 272 | 23 | CH₃CO | Gemcitabine (15%) | OC4H8Ph (60%) |
| 7 | CH₃ | 272 | 26 | CH₃CO | Gemcitabine (30%) | OBzl (50%) |
| 8 | CH₃ | 272 | 26 | CH₃CO | Gemcitabine (30%) | Phe-OBzl (40%) |
| 9 | CH₃ | 272 | 26 | CH₃CO | Gemcitabine (25%) | Phe-OBzl (50%) |
| 10 | CH₃ | 272 | 26 | CH₃CO | Gemcitabine (15%) | Phe-OBzl (60%) |
| 11 | CH₃ | 272 | 26 | CH₃CO | Gemcitabine (15%) | Val-OBzl (60%) |
| 12 | CH₃ | 272 | 26 | CH₃CO | Gemcitabine (25%) | OC4H8Ph (40%) |
| 13 | CH₃ | 272 | 26 | CH₃CO | Gemcitabine (20%) | OC4H8Ph (50%) |
| 14 | CH₃ | 272 | 26 | CH₃CO | Gemcitabine (15%) | OC4H8Ph (60%) |
| 15 | CH₃ | 272 | 32 | CH₃CO | Gemcitabine (30%) | Phe-OBzl (40%) |
| 16 | CH₃ | 272 | 32 | CH₃CO | Gemcitabine (30%) | Phe-OBzl (50%) |
| 17 | CH₃ | 272 | 32 | CH₃CO | Gemcitabine (20%) | Phe-OBzl (60%) |

TABLE 1-continued

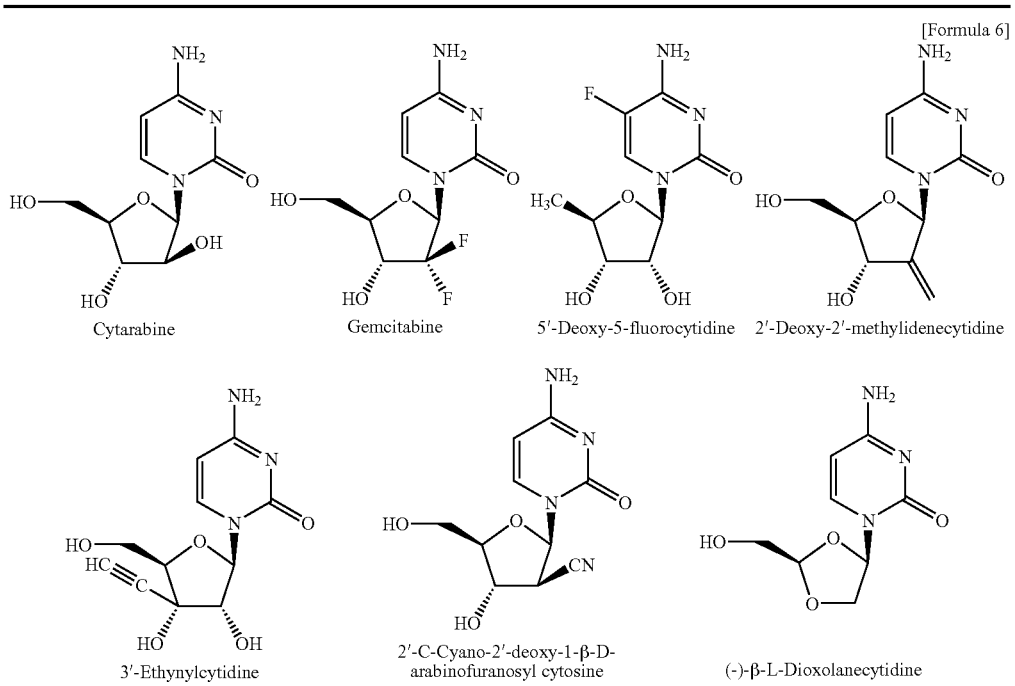

| No. | R | n (mean) | m (mean) | A | X: Cytidine Antimetabolite (percentage) | X: Hydrophobic Substituent (percentage) |
|---|---|---|---|---|---|---|
| 18 | CH₃ | 272 | 32 | CH₃CO | Gemcitabine (15%) | Val-OBzl (60%) |
| 19 | CH₃ | 272 | 32 | CH₃CO | Gemcitabine (15%) | OC4H8Ph (60%) |
| 20 | CH₃ | 272 | 35 | CH₃CO | Gemcitabine (15%) | OC4H8Ph (55%) |
| 21 | CH₃ | 272 | 26 | CH₃CO | 5'-Deoxy-5-fluorocytidine (15%) | Phe-OBzl (60%) |
| 22 | CH₃ | 272 | 26 | CH₃CO | 5'-Deoxy-5-fluorocytidine (15%) | OC4H8Ph (60%) |
| 23 | CH₃ | 272 | 26 | CH₃CO | 2'-Deoxy-2'-methylidenecytidine (15%) | Phe-OBzl (60%) |
| 24 | CH₃ | 272 | 26 | CH₃CO | 2'-Deoxy-2'-methylidenecytidine (15%) | OC4H8Ph (60%) |
| 25 | CH₃ | 272 | 26 | CH₃CO | 3'-Ethynylcytidine (15%) | Phe-OBzl (60%) |
| 26 | CH₃ | 272 | 26 | CH₃CO | 3'-Ethynylcytidine (15%) | OC4H8Ph (60%) |
| 27 | CH₃ | 272 | 26 | CH₃CO | 2'-C-Cyano-2'-deoxy-1-β-D-arabinofuranosyl cytosine (15%) | Phe-OBzl (60%) |
| 28 | CH₃ | 272 | 26 | CH₃CO | 2'-C-Cyano-2'-deoxy-1-β-D-arabinofuranosyl cytosine (15%) | OC4H8Ph (60%) |
| 29 | CH₃ | 272 | 26 | CH₃CO | (−)-β-L-Dioxolanecytidine (15%) | Phe-OBzl (60%) |
| 30 | CH₃ | 272 | 26 | CH₃CO | (−)-β-L-Dioxolanecytidine (15%) | OC4H8Ph (60%) |

By way of particular non-limiting example, the polymeric derivative of a cytidine antimetabolite according to the present invention can be produced by condensing, using a dehydration condensation agent in an organic solvent, a cytidine antimetabolite with the methoxypolyethylene glycol-polyglutamic acid block copolymer prepared according to the method described in Patent Document 3.

The solvent used in the above reaction is not particularly limited provided that it allows the reaction to proceed; however, examples thereof include an aromatic hydrocarbon such as toluene and xylene, a halogenated hydrocarbon such as methylene chloride, chloroform and 1,2-dichloroethane, an ether such as tetrahydrofuran, dioxane, dimethoxyethane and diethylene glycol dimethyl ether, a nitrile such as acetonitrile and propionitrile, an amide such as dimethylformamide, dimethylacetamide and N-methylpyrrolidone, a urea such as 1,3-dimethylimidazolidinone, and a mixed solvent thereof. The amide or the urea is preferable; more preferred is dimethylformamide or 1,3-dimethylimidazolidinone.

The dehydration condensation agent used in the above reaction is not particularly limited provided that it allows the proceeding of the condensation reaction of an amino group at the 4-position of a cytidine antimetabolite with the carboxyl group; however, preferred examples thereof include DMT-MM(4-(4,6-dimethoxy-1,3,5-triazin-2-yl)-4-methylmorpholinium chloride) and 2-ethoxy-1-ethoxycarbonyl-1,2-dihydroquinoline.

The reaction temperature in the above reaction is typically 4 to 60° C., preferably 15 to 50° C.

After the above reaction, a separation means known per se can be properly applied such as, for example, vacuum concentration, solvent extraction, crystallization, dialysis and chromatography, if necessary, to isolate and purify a desired compound.

By the above method, a polymeric derivative can be obtained in which X consists of a cytidine antimetabolite residue alone or of a cytidine antimetabolite residue and a hydroxyl group.

When the polymeric derivative of a cytidine antimetabolite according to the present invention has a hydrophobic substituent, the derivative can be produced by condensing, using a dehydration condensation agent in an organic solvent, an amino group of a cytidine antimetabolite with an unsubstituted carboxyl group in a side chain of a polymeric compound composed of the following polyethylene glycol moiety and a polymer moiety having carboxyl groups in the side chains which is obtained by introducing a hydrophobic substituent into a part of the carboxyl groups of the methoxypolyethylene glycol-polyglutamic acid block copolymer prepared, for example, according to the method described in Patent Document 3.

The hydrophobic substituent is introduced in the following way. For example, when the hydrophobic substituent is an alkoxy group, the introduction is performed by condensing a corresponding alcohol with the carboxyl group (esterification) using a dehydration condensation agent in a solvent or by subjecting a corresponding alkyl halide or the like and the carboxyl group to nucleophilic substitution reaction in the presence of a base in a solvent. For example, when the hydrophobic substituent is a substituted amino group, the derivative having the substituent can be produced by condensing a corresponding amine with the carboxyl group (amidation) using a dehydration condensation agent in a solvent.

The solvent used in the above dehydration condensation (esterification) is not particularly limited provided that it allows the reaction to proceed. However, the same solvent can be used as that usable in the dehydration condensation of the above methoxypolyethylene glycol-polyglutamic acid block copolymer with a cytidine antimetabolite; a preferable solvent is also the same as above. The dehydration condensation agent is not particularly limited provided that it allows the proceeding of the dehydration condensation of an alcohol with a carboxyl group; however, preferred is dicyclohexylcarbodiimide, diisopropylcarbodiimide, 1-dimethylaminopropyl-3-ethylcarbodiimide, carbonyldiimidazole, isobutyl chloroformate, or pivalic acid chloride.

A reaction aid may be used in the dehydration condensation reaction; examples thereof include N-hydroxysuccinimide, 1-hydroxybenzotriazole, 4-dimethylaminopyridine and 2,6-di-t-butyl-4-methylpyridine.

The reaction temperature in the dehydration condensation reaction is typically 4 to 60° C., preferably 15 to 50° C. The reaction time is 2 hours to several days, preferably 4 to 48 hours.

The solvent used in the above nucleophilic substitution reaction is not particularly limited provided that it allows the reaction to proceed. However, the same solvent can be used as that usable in the dehydration condensation of the above methoxypolyethylene glycol-polyglutamic acid block copolymer with a cytidine antimetabolite; a preferable solvent is also the same as above. Examples of the base include an alkali metal carbonate such as lithium carbonate, sodium carbonate and potassium carbonate; an alkali metal hydride such as lithium hydride, sodium hydride and potassium hydride; an alkali metal hydroxide such as lithium hydroxide, sodium hydroxide and potassium hydroxide; an alkali metal alkoxide such as lithium methoxide, sodium methoxide, sodium ethoxide and potassium tert-butoxide; and an organic amine such as triethylamine, tributylamine, N,N-diisopropylethylamine, N-methylmorpholine, pyridine, 4-(N,N-dimethylamino)pyridine, N,N-dimethylaniline, N,N-diethylaniline, 1,5-diazabicyclo[4.3.0]nona-5-ene, 1,4-diazabicyclo[2.2.2]octane (DABCO) and 1,8-diazabicyclo[5.4.0]-7-undecene (DBU); preferred is an organic amine.

The reaction temperature in the above nucleophilic substitution reaction is typically 4 to 60° C., preferably room temperature to 50° C. The reaction time is one hour to several days, preferably 4 to 48 hours.

The solvent used in the above dehydration condensation reaction (amidation reaction) is not particularly limited provided that it allows the reaction to proceed. However, the same solvent can be used as that usable in the dehydration condensation of the above methoxypolyethylene glycol-polyglutamic acid block copolymer with a cytidine antimetabolite; a preferable solvent is also the same as above. The dehydration condensation agent is not particularly limited provided that it allows the proceeding of the dehydration condensation of an amine with a carboxyl group; however, preferred is dicyclohexylcarbodiimide, diisopropylcarbodiimide, 1-dimethylaminopropyl-3-ethylcarbodiimide, carbonyldiimidazole, isobutyl chloroformate, pivalic acid chloride, DMT-MM(4-(4,6-dimethoxy-1,3,5-triazin-2-yl)-4-methylmorpholinium chloride), TFFH (tetramethylfluoroformamidinium hexafluorophosphate), or BOP (benzotriazol-1-yloxytris(dimethylamino)phosphonium hexafluorophosphate).

A reaction aid may be used in the dehydration condensation reaction; examples thereof include N-hydroxysuccinimide, 1-hydroxybenzotriazole, 4-dimethylaminopyridine and 2,6-di-t-butyl-4-methylpyridine.

The reaction temperature in the dehydration condensation reaction is typically 4 to 60° C., preferably room temperature to 50° C. The reaction time is one hour to several days, preferably 4 to 48 hours.

Since the reaction sequence for binding the hydrophobic substituent and the cytidine antimetabolite to the polymeric compound does not matter, they may be mixed for reaction. However, the hydrophobic substituent is preferably introduced into the polymeric carrier before binding the cytidine antimetabolite thereto to avoid the reaction and decomposition of the antimetabolite as the body for activity having a multifunctional group.

The polymeric derivative of a cytidine antimetabolite according to the present invention may form micelles having shells of the polyethylene glycol moiety in water. The formation of the micelles can be identified, for example, by gel filtration chromatography (GPC) or dynamic light scattering.

According to the present invention, the formation of the micelles is facilitated by the binding of the carboxyl group, which is not bonded to the cytidine antimetabolite, to the hydrophobic substituent.

The present invention encompasses an antitumor or antiviral agent comprising the above-described polymeric derivative of a cytidine antimetabolite as a medicinal ingredient. The polymeric derivative of a cytidine antimetabolite may be administered as it is or in the form of a pharmaceutical composition in which it is mixed with pharmaceutically acceptable substances. The dosage form of the pharmaceutical composition may be any dosage form such as an injection, a powder, a granule, a tablet and a suppository. These preparations may also contain various auxiliary substances for pharmaceutical use, i.e., a carrier and other auxiliaries including additives such as a stabilizer, a preservative, a soothing agent and an emulsifier.

The content of the polymeric derivative of a cytidine antimetabolite in a preparation variously varies depending on the preparation; however, it is typically 0.1 to 100% by weight, preferably 1 to 98% by weight.

The indication of the antitumor agent of the present invention comprising the polymeric derivative of a cytidine antimetabolite as a medicinal ingredient is not particularly limited; however, the agent can be used for cancers such as, for example, non-small-cell lung cancer, pancreas cancer, stomach cancer, colon cancer, rectal cancer, breast cancer, ovary cancer, bladder cancer and AIDS-associated Kaposi's sarcoma.

The indication of the antiviral agent of the present invention comprising the polymeric derivative of a cytidine antimetabolite as a medicinal ingredient is not particularly limited; however, the agent can be used, for example, for acquired immune deficiency syndrome (AIDS), herpes zoster, herpes simplex virus infectious disease, and the like and can also be employed for the purpose of preventing infection.

The polymeric derivative of a cytidine antimetabolite according to the present invention can be administered by any method including oral administration, injection, intrarectal administration, intraportal administration, mixing into an organ perfusate, and local administration into an affected organ. However, preferred is parenteral administration; more preferred is intravenous or intraarterial administration by injection or local administration into an affected organ. The dosage of the polymeric derivative of a cytidine antimetabolite according to the present invention varies depending on the disease state, the method of administration, the condition, age and body weight of a patient, and the like; however, it is typically 1 mg to 5,000 mg, preferably 10 mg to 2,000 mg, per $m^2$ of body surface area, which may be administered once or in several portions per day. The administration may be carried out daily, or repeatedly several days to several months apart. An administration method, dosage and administration schedule other than the above may be used as needed.

The polymeric derivative of the present invention also includes that in which a prodrug is bound. Here, the prodrug is a chemical derivative of a biologically active parent compound, which releases the parent compound in vivo when administered.

EXAMPLES

The present invention is described below in further detail with reference to Examples, Reference Examples and Test Examples. However, the scope of the invention is not intended to be limited thereto.

Reference Example 1

Synthesis of N-Acetylated Block Copolymer of Monomethoxypolyethylene Glycol Having Molecular Weight of about 12,000 with Polyglutamic Acid Having Polymerization Number of about 26

A polyethylene glycol having a methoxy group at one end and a 3-aminopropyl group at the other end (SUNBRIGHT MEPA-12T from NOF Corporation, average molecular weight: 12,000, 16 g) was dissolved in dimethyl sulfoxide (320 mL), to which γ-benzyl-L-glutamate N-carboxylic anhydride (BLG-NCA, 9.48 g; 27 equivalents based on the polyethylene glycol) was then added, followed by stirring at 30° C. overnight. The reaction solution was dropwise added to an isopropyl ether-ethanol mixed solvent (4:1, 6.4 L) under stirring, which was then stirred for further 3 hours. The precipitated deposit was collected by filtration and washed with an isopropyl ether-ethanol mixed solvent (4:1, 400 mL). The resultant product (22.78 g) was dissolved in N,N-dimethylformamide (370 mL), to which acetic anhydride (6.83 mL) was then added, followed by stirring at 20° C. overnight. The resultant solution was dropwise added to an isopropyl ether-ethyl acetate mixed solvent (4:1, 3.7 L) under stirring, which was then stirred for further 3 hours. The precipitated deposit was collected by filtration and washed with an isopropyl ether-ethyl acetate mixed solvent (4:1, 300 mL). The resultant product (22.92 g) was dissolved in N,N-dimethylformamide (370 mL), to which 5% palladium carbon (containing 55% water, 2.50 g) was then added, followed by stirring at 30° C. in a hydrogen atmosphere for 4 hours and then at room temperature overnight. After filtering off the palladium carbon, the filtrate was dropwise added to an isopropyl ether-ethyl acetate mixed solvent (4:1, 5 L) under stirring, which was then stirred for further one hour. The precipitated deposit was collected by filtration and washed with an isopropy ether-ethyl acetate mixed solvent (4:1, 300 mL). The resultant product (16 g) was dissolved in distilled water (800 mL), to which a 1 M sodium hydroxide aqueous solution was then added to adjust the pH of the solution to 11. Distilled water was added thereto so as to provide a final solution volume of 1,600 mL, followed by adding sodium chloride (80 g). This solution was passed through a column of the adsorption resin HP-20ss (from Mitsubishi Chemical Corporation, 500 mL); the column was washed with a 5% sodium chloride aqueous solution (2,000 mL) and distilled water (20,000 mL) and then eluted with a 50% acetonitrile aqueous solution (2,500 mL). The eluted fraction containing the desired compound was passed through and eluted from a column of the cation exchange resin Dowex 50W (from The Dow Chemical Company, proton-type, 100 mL); the column was further eluted with 50% aqueous acetonitrile (150 mL). The eluted fraction containing the desired compound was concentrated under reduced pressure until the solution volume reaches about 300 mL, and then subjected to freeze-drying to provide the title compound (15.84 g).

The average polymerization number of glutamic acid (the number of carboxylic acids) in one molecule of the compound was 26.22, based on the titration value obtained using a sodium hydroxide aqueous solution.

Reference Example 2

Synthesis of N-Acetylated Block Copolymer of Monomethoxypolyethylene Glycol Having Molecular Weight of about 12,000 with Polyglutamic Acid Having Polymerization Number of about 41

According to the method described in Reference Example 1, 45 equivalents of BLG-NCA was used based on the polyethylene glycol to provide the title compound.

The average polymerization number of glutamic acid (the number of carboxylic acids) in one molecule of the compound was 41.45, based on the titration value obtained using a sodium hydroxide aqueous solution.

Reference Example 3

Synthesis of N-Acetylated Block Copolymer of Monomethoxypolyethylene Glycol Having Molecular Weight of about 12,000 with Polyglutamic Acid Having Polymerization Number of about 24

According to the method described in Reference Example 1, 25 equivalents of BLG-NCA was used based on the polyethylene glycol to provide the title compound.

The average polymerization number of glutamic acid (the number of carboxylic acids) in one molecule of the compound was 23.70, based on the titration value obtained using a sodium hydroxide aqueous solution.

Reference Example 4

Synthesis of N-Acetylated Block Copolymer of Monomethoxypolyethylene Glycol Having Molecular Weight of about 12,000 with Polyglutamic Acid Having Polymerization Number of about 32

According to the method described in Reference Example 1, 35 equivalents of BLG-NCA was used based on the polyethylene glycol to provide the title compound.

The average polymerization number of glutamic acid (the number of carboxylic acids) in one molecule of the compound was 31.71, based on the titration value obtained using a sodium hydroxide aqueous solution.

Reference Example 5

Synthesis of N-Acetylated Block Copolymer of Monomethoxypolyethylene Glycol Having Molecular Weight of about 12,000 with Polyglutamic Acid Having Polymerization Number of about 36

According to the method described in Reference Example 1, 40 equivalents of BLG-NCA was used based on the polyethylene glycol to provide the title compound.

The average polymerization number of glutamic acid (the number of carboxylic acids) in one molecule of the compound was 35.90, based on the titration value obtained using a sodium hydroxide aqueous solution.

Reference Example 6

Synthesis of N-Acetylated Block Copolymer of Monomethoxypolyethylene Glycol Having Molecular Weight of about 12,000 with Polyglutamic Acid Having Polymerization Number of about 21

According to the method described in Reference Example 1, 23 equivalents of BLG-NCA was used based on the polyethylene glycol to provide the title compound.

The average polymerization number of glutamic acid (the number of carboxylic acids) in one molecule of the compound was 21.38, based on the titration value obtained using a sodium hydroxide aqueous solution.

Reference Example 7

Synthesis of N-Acetylated Block Copolymer of Monomethoxypolyethylene Glycol Having Molecular Weight of about 12,000 with Polyglutamic Acid Having Polymerization Number of about 26

According to the method described in Reference Example 1, 30 equivalents of BLG-NCA was used based on the polyethylene glycol to provide the title compound.

The average polymerization number of glutamic acid (the number of carboxylic acids) in one molecule of the compound was 26.48, based on the titration value obtained using a sodium hydroxide aqueous solution.

Reference Example 8

Synthesis of Amide Conjugate of L-Phenylalanine Benzyl Ester with N-Acetylated Block Copolymer of Monomethoxypolyethylene Glycol Having Molecular Weight of about 12,000 with Polyglutamic Acid Having Polymerization Number of about 24

The N-acetylated block copolymer of a monomethoxypolyethylene glycol having a molecular weight of about 12,000 with a polyglutamic acid having a polymerization number of about 24 (1.533 g) described in Reference Example 3 was dissolved in N,N-dimethylformamide (32 mL), to which L-phenylalanine benzyl ester 4-toluenesulfonate (0.464 g), TFFH (0.286 g), N,N-diisopropylethylamine (0.672 mL) and 2,6-di-t-butyl-4-methylpyridine (0.495 g) were then added, followed by stirring the mixture at 37° C. for 20 hours. The reaction solution was cooled to room temperature and then diluted with ethanol (64 mL), to which diisopropyl ether (256 mL) was then added dropwise under stirring. After 30 minutes of stirring, the precipitated deposit was collected by filtration and washed with a diisopropyl ether-ethanol mixed solvent (4:1). The resultant product was dissolved in 30% aqueous acetonitrile (45 mL), which was then dialyzed with distilled water (2 L×3) using a dialysis membrane (molecular cutoff of 12,000 to 14,000). Acetonitrile (15 mL) was added to the dialyzed solution, and the mixture was passed through the cation exchange resin Dowex 50W (proton-type), which was eluted with 50% aqueous acetonitrile. The eluted fraction containing the desired compound was concentrated under reduced pressure to ½ volume and subjected to freeze-drying to provide the title compound (1.689 g).

After hydrolyzing the compound, the released benzyl alcohol was quantitated by high performance liquid chromatography (HPLC) to determine the amide-bonding rate of the Phe-OBzl group in the compound. As a result, the bonding rate was 32.8% based on the carboxyl groups of the polyglutamic acid.

Method of Hydrolysis

The title compound (34.48 mg) was dissolved in methanol (1 mL), to which a 0.5 M sodium hydroxide aqueous solution (1 mL) was then added, followed by stirring at 40° C. for one hour. The solution was neutralized with acetic acid and then diluted with distilled water to make an exact 5 mL of solution.

Analysis Conditions of HPLC (Analysis of Benzyl Alcohol)

Column: Inertsil ODS-3 (particle size: 5 μm), 4.6ϕ×150 mm;

Column temperature: 40° C.;

Eluent: solution A: 1% phosphoric acid aqueous solution, solution B: acetonitrile;

Gradient: % solution B (time: minutes) 30 (O), 80 (10);

Flow rate: 1 mL/min.;

Detector (detection wavelength): UV (260 nm)

Reference Example 9

Synthesis of Amide Conjugate of L-Phenylalanine Benzyl Ester with N-Acetylated Block Copolymer of Monomethoxypolyethylene Glycol Having Molecular Weight of about 12,000 with Polyglutamic Acid Having Polymerization Number of about 41

The N-acetylated block copolymer of a monomethoxypolyethylene glycol having a molecular weight of about 12,000 with a polyglutamic acid having a polymerization number of about 41 (176.5 mg) described in Reference Example 2 was dissolved in N,N-dimethylformamide (5.3 mL), to which L-phenylalanine benzyl ester 4-toluenesulfonate (63.0 mg), TFFH (38.9 mg), N,N-diisopropylethylamine (117.3 µL) and 2,6-di-t-butyl-4-methylpyridine (87.0 mg) were then added, followed by stirring the mixture at 37° C. for 22 hours. The reaction solution was cooled to room temperature and then diluted with ethanol (10.6 mL), to which diisopropyl ether (42.4 mL) was then added dropwise under stirring. After 30 minutes of stirring, the precipitated deposit was collected by filtration and washed with a diisopropyl ether-ethanol mixed solvent (4:1). The resultant product was dissolved in 20% aqueous acetonitrile (16 mL), which was then dialyzed with distilled water (2 L×3) using a dialysis membrane (molecular cutoff of 12,000 to 14,000). The dialyzed solution was passed through the cation exchange resin Dowex 50W (proton-type, 9 mL), which was eluted with 50% aqueous acetonitrile. The eluted fraction containing the desired compound was subjected to freeze-drying to provide the title compound (194.0 mg).

After hydrolyzing the compound in the same way as that in Reference Example 8, the released benzyl alcohol was quantitated by high performance liquid chromatography (HPLC) under the same conditions as those in Reference Example 8 to determine the amide-bonding rate of the Phe-OBzl group in the compound. As a result, the bonding rate was 32.6% based on the carboxyl groups of the polyglutamic acid.

Reference Example 10

Synthesis of Amide Conjugate of L-Phenylalanine Benzyl Ester with N-Acetylated Block Copolymer of Monomethoxypolyethylene Glycol Having Molecular Weight of about 12,000 with Polyglutamic Acid Having Polymerization Number of about 32

The N-acetylated block copolymer of a monomethoxypolyethylene glycol having a molecular weight of about 12,000 with a polyglutamic acid having a polymerization number of about 32 (668 mg) described in Reference Example 4 was dissolved in N,N-dimethylformamide (13 mL), to which L-phenylalanine benzyl ester 4-toluenesulfonate (282 mg), TFFH (175 mg) and N,N-diisopropylethylamine (345 µL) were then added, followed by stirring the mixture at 40° C. for 20 hours. The reaction solution was cooled to room temperature and then diluted with ethanol (26 mL), to which diisopropyl ether (104 mL) was then added dropwise under stirring. The precipitated deposit was collected by filtration and washed with a diisopropyl ether-ethanol mixed solvent (4:1). The resultant product was dissolved in 50% aqueous acetonitrile (16 mL), which was then dialyzed with distilled water (2 L×3) using a dialysis membrane (molecular cutoff of 12,000 to 14,000). The dialyzed solution was passed through the cation exchange resin Dowex 50W (proton-type, 10 mL), which was eluted with 50% aqueous acetonitrile. The eluted fraction containing the desired compound was subjected to freeze-drying to provide the title compound (762 mg).

After hydrolyzing the compound in the same way as that in Reference Example 8, the released benzyl alcohol was quantitated by high performance liquid chromatography (HPLC) under the same conditions as those in Reference Example 8 to determine the amide-bonding rate of the Phe-OBzl group in the compound. As a result, the bonding rate was 41.8% based on the carboxyl groups of the polyglutamic acid.

Reference Example 11

Synthesis of Amide Conjugate of L-Valine Benzyl Ester with N-Acetylated Block Copolymer of Monomethoxypolyethylene Glycol Having Molecular Weight of about 12,000 with Polyglutamic Acid Having Polymerization Number of about 36

The N-acetylated block copolymer of a monomethoxypolyethylene glycol having a molecular weight of about 12,000 with a polyglutamic acid having a polymerization number of about 36 (531 mg) described in Reference Example 5 was dissolved in N,N-dimethylformamide (10.6 mL), to which L-valine benzyl ester 4-toluenesulfonate (195 mg), TFFH (135 mg) and N,N-diisopropylethylamine (288 µL) were then added, followed by stirring the mixture at 40° C. for 30 hours. The reaction solution was cooled to room temperature and then diluted with ethanol (20 mL), to which diisopropyl ether (80 mL) was then added dropwise under stirring. After 30 minutes of stirring, the precipitated deposit was collected by filtration and washed with a diisopropyl ether-ethanol mixed solvent (4:1). The resultant product was dissolved in 30% aqueous acetonitrile (25 mL), which was then dialyzed with distilled water (2 L×3) using a dialysis membrane (molecular cutoff of 12,000 to 14,000). The cation exchange resin Dowex 50W (proton-type, 3 mL) was added to the dialyzed solution, which was stirred for 30 minutes, followed by filtering off the resin. The filtrate containing the desired compound was subjected to freeze-drying to provide the title compound (559 mg).

After hydrolyzing the compound in the same way as that in Reference Example 8, the released benzyl alcohol was quantitated by high performance liquid chromatography (HPLC) under the same conditions as those in Reference Example 8 to determine the amide-bonding rate of the Val-OBzl group in the compound. As a result, the bonding rate was 41.3% based on the carboxyl groups of the polyglutamic acid.

Reference Example 12

Synthesis of Amide Conjugate of L-Phenylalanine Benzyl Ester with N-Acetylated Block Copolymer of Monomethoxypolyethylene Glycol Having Molecular Weight of about 12,000 with Polyglutamic Acid Having Polymerization Number of about 26

The N-acetylated block copolymer of a monomethoxypolyethylene glycol having a molecular weight of about 12,000 with a polyglutamic acid having a polymerization number of about 26 (6.00 g) described in Reference Example 1 was dissolved in N,N-dimethylformamide (150 mL), to which L-phenylalanine benzyl ester hydrochloride (2.08 g), DMT-MM (2.37 g) and N,N-diisopropylethylamine (1.24 mL) were then added, followed by stirring the mixture at 40° C. overnight. The reaction solution was cooled to room temperature and then dropwise added to a diisopropyl ether-ethanol mixed solvent (4:1, 1,500 mL). After 30 minutes of stirring, the precipitated deposit was collected by filtration and washed with a diisopropyl ether-ethanol mixed solvent (4:1). The resultant product was dissolved in 97 weight % aqueous DMF (150 mL), to which the cation exchange resin Dowex 50W (proton-type, 15 mL) was added before stirring the mixture at room temperature for 2 hours, followed by filtering off the resin and washing the resin with DMF (75 mL). The resultant filtrate was dropwise added to a diisopropyl ether-ethanol mixed solvent (4:1) (2,400 mL), which was stirred for 30 minutes, followed by collecting the precipitated deposit by filtration to provide the title compound (6.88 g).

After hydrolyzing the compound in the same way as that in Reference Example 8, the released benzyl alcohol was quantitated by high performance liquid chromatography (HPLC) under the same conditions as those in Reference Example 8 to determine the amide-bonding rate of the Phe-OBzl group in the compound. As a result, the bonding rate was 62.4% based on the carboxyl groups of the polyglutamic acid.

Reference Example 13

Synthesis of Ester Conjugate of Benzyl Bromide with N-Acetylated Block Copolymer of Monomethoxypolyethylene Glycol Having Molecular Weight of about 12,000 with Polyglutamic Acid Having Polymerization Number of about 26

The N-acetylated block copolymer of a monomethoxypolyethylene glycol having a molecular weight of about 12,000 with a polyglutamic acid having a polymerization number of about 26 (342 mg) described in Reference Example 1 was dissolved in N,N-dimethylformamide (6.8 mL), to which benzyl bromide (29.0 µL) and N,N-diisopropylethylamine (53.1 µL) were then added, followed by stirring the mixture at 37° C. overnight. The reaction solution was cooled to room temperature and then diluted with ethanol (13.6 mL), to which diisopropyl ether (54.4 mL) was then added dropwise under stirring. After one hour of stirring, the precipitated deposit was collected by filtration and washed with a diisopropyl ether-ethanol mixed solvent (4:1). The resultant product was dissolved in 50% aqueous acetonitrile (20 mL), and the solution was passed through the cation exchange resin Dowex 50W (proton-type, 4 mL), which was then eluted with 50% aqueous acetonitrile. The eluted fraction containing the desired compound was concentrated under reduced pressure to ½ volume and then subjected to freeze-drying to provide the title compound (352 mg).

After hydrolyzing the compound in the same way as that in Reference Example 8, the released benzyl alcohol was quantitated by high performance liquid chromatography (HPLC) under the same conditions as those in Reference Example 8 to determine the bonding rate of the OBzl group in the compound. As a result, the bonding rate was 25.0% based on the carboxyl groups of the polyglutamic acid.

Reference Example 14

Synthesis of Ester Conjugate of 4-Phenylbutyl Bromide with N-Acetylated Block Copolymer of Monomethoxypolyethylene Glycol Having Molecular Weight of about 12,000 with Polyglutamic Acid Having Polymerization Number of about 26

The N-acetylated block copolymer of a monomethoxypolyethylene glycol having a molecular weight of about 12,000 with a polyglutamic acid having a polymerization number of about 26 (2.33 g) described in Reference Example 7 was dissolved in N,N-dimethylformamide (50 mL), to which 4-phenylbutyl bromide (682 mg) and 1,8-diazabicyclo[5.4.0]-7-undecene (DBU, 598 µL) were then added, followed by stirring the mixture at 38° C. overnight. The reaction solution was cooled to room temperature and then dropwise added to a diisopropyl ether-ethanol mixed solvent (4:1, 500 mL). After one hour of stirring, the precipitated deposit was collected by filtration and washed with a diisopropyl ether-ethanol mixed solvent (4:1). The resultant product was dissolved in 50% aqueous acetonitrile, to which the cation exchange resin Dowex 50W (proton-type, 5 mL) was added before stirring the mixture for 2 hours, followed by filtering off the resin and then subjecting the filtrate to freeze-drying to provide the title compound (2.54 g).

After hydrolyzing the compound in the same way as that in Reference Example 8, the released 4-phenylbutanol was quantitated by high performance liquid chromatography (HPLC) to determine the bonding rate of the 4-phenylbutoxy group in the compound. As a result, the bonding rate was 65.7% based on the carboxyl groups of the polyglutamic acid.

Example 1

Polymeric Derivative of Cytidine Antimetabolite of Formula (1) wherein R is Methyl Group; A is Acetyl Group; Average of n is 272; Average of m is 21; and X is Gemcitabine or Hydroxyl Group N,N-Dimethylformamide (15 mL) and N,N-diisopropylethylamine (192 µL) were added to the N-acetylated block copolymer of a monomethoxypolyethylene glycol having a molecular weight of about 12,000 with a polyglutamic acid having a polymerization number of about 21 (759 mg) described in Reference Example 6 and gemcitabine hydrochloride (330 mg), which was then stirred at 37° C. After dissolution, 2-ethoxy-1-ethoxycarbonyl-1,2-dihydroquinoline (EEDQ, 300 mg) was added thereto, which was stirred at 37° C. for 20 hours. The reaction solution was cooled to room temperature and then diluted with ethanol (30 mL), to which diisopropyl ether (120 mL) was dropwise added under stirring. After one hour of stirring, the precipitated deposit was collected by filtration and washed with a diisopropyl ether-ethanol mixed solvent (4:1). The resultant product was dissolved in 25% aqueous acetonitrile (40 mL), which was then dialyzed with distilled water (2 L×3) using a dialysis membrane (molecular cutoff of 12,000 to 14,000). The dialyzed solution was subjected to freeze-drying to provide the title compound (1,078 mg).

After hydrolyzing the compound, the released gemcitabine was quantitated by high performance liquid chromatography (HPLC) to determine the gemcitabine content of the compound. As a result, the content was 20.8% (w/w) (58.0% based on the carboxyl groups of the polycarboxylic acid) in terms of gemcitabine hydrochloride. In addition, when the compound of the present invention was subjected to HPLC analysis, the content of free gemcitabine was 0.3% or less.

Method of Hydrolysis

The title compound (3.60 mg) was dissolved in methanol (0.5 mL), to which concentrated ammonia water (0.5 mL) was then added before sealing, followed by stirring at 37° C. for one hour. The solution was neutralized with acetic acid and then diluted with distilled water to make an exact 10 mL of solution.

Analysis Conditions of HPLC (Analysis of Gemcitabine)
Column: Inertsil ODS-3 (particle size: 5 μm), 4.6φ×150 mm;
Column temperature: 40° C.;
Eluent: 95% phosphate buffer (10 mM, pH 6.9)-5% acetonitrile;
Flow rate: 1 mL/min.;
Detector (detection wavelength): UV (275 nm)

Example 2

Polymeric Derivative of Cytidine Antimetabolite of Formula (1) wherein R is Methyl Group; A is Acetyl Group; Average of n is 272; Average of m is 24; and X is Gemcitabine, Hydroxyl Group or L-Phenylalanine Benzyl Ester Residue N,N-Dimethylformamide (26 mL) and N,N-diisopropylethylamine (0.213 mL) were added to the compound (1.298 g) described in Reference Example 8 and gemcitabine hydrochloride (0.366 g), which was then stirred at 37° C. After dissolution, 2-ethoxy-1-ethoxycarbonyl-1,2-dihydroquinoline (EEDQ, 0.362 g) was added thereto, which was stirred at 37° C. overnight. The reaction solution was cooled to room temperature and then diluted with ethanol (52 mL), to which diisopropyl ether (208 mL) was dropwise added under stirring. After one hour of stirring, the precipitated deposit was collected by filtration and washed with a diisopropyl ether-ethanol mixed solvent (4:1). The resultant product was dissolved in 25% aqueous acetonitrile (40 mL), which was then dialyzed with distilled water (2 L×3) using a dialysis membrane (molecular cutoff of 12,000 to 14,000). The dialyzed solution was subjected to freeze-drying to provide the title compound (1.330 g).

After hydrolyzing the compound in the same way as that in Example 1, the released gemcitabine was quantitated by high performance liquid chromatography (HPLC) under the same conditions as those in Example 1 to determine the gemcitabine content of the compound. As a result, the content was 10.7% (w/w) (28.1% based on the carboxyl groups of the polycarboxylic acid) in terms of gemcitabine hydrochloride. In addition, when the compound was subjected to HPLC analysis, the content of free gemcitabine was 0.3% or less.

Example 3

Polymeric Derivative of Cytidine Antimetabolite of Formula (1) wherein R is Methyl Group; A is Acetyl Group; Average of n is 272; Average of m is 41; and X is Gemcitabine, Hydroxyl Group or L-Phenylalanine Benzyl Ester Residue N,N-Dimethylformamide (3.3 mL) and N,N-diisopropylethylamine (39.2 μL) were added to the compound (165 mg) described in Reference Example 9 and gemcitabine hydrochloride (67.4 mg), which was then stirred at 37° C. After dissolution, 2-ethoxy-1-ethoxycarbonyl-1,2-dihydroquinoline (EEDQ, 56.0 mg) was added thereto, which was then stirred at 37° C. for 23 hours. The reaction solution was cooled to room temperature and then diluted with ethanol (6.6 mL), to which diisopropyl ether (26.4 mL) was dropwise added under stirring. After 30 minutes of stirring, the precipitated deposit was collected by filtration and washed with a diisopropyl ether-ethanol mixed solvent (4:1). The resultant product was dissolved in 10% aqueous acetonitrile (16 mL), which was then dialyzed with distilled water (2 L×3) using a dialysis membrane (molecular cutoff of 12,000 to 14,000). The dialyzed solution was subjected to freeze-drying to provide the title compound (183 mg).

After hydrolyzing the compound in the same way as that in Example 1, the released gemcitabine was quantitated by high performance liquid chromatography (HPLC) under the same conditions as those in Example 1 to determine the gemcitabine content of the compound of the present invention. As a result, the content was 21.2% (w/w) (42.6% based on the carboxyl groups of the polycarboxylic acid) in terms of gemcitabine hydrochloride. In addition, when the compound was subjected to HPLC analysis, the content of free gemcitabine was 0.3% or less.

Example 4

Polymeric Derivative of Cytidine Antimetabolite of Formula (1) wherein R is Methyl Group; A is Acetyl Group; Average of n is 272; Average of m is 26; and X is Gemcitabine, Hydroxyl Group or Benzyloxy Group N,N-Dimethylformamide (6 mL) and N,N-diisopropylethylamine (63.1 μL) were added to the compound (295 mg) described in Reference Example 13 and gemcitabine hydrochloride (108.5 mg), which was then stirred at 37° C. After dissolution, 2-ethoxy-1-ethoxycarbonyl-1,2-dihydroquinoline (EEDQ, 98.2 mg) was added thereto, which was stirred at 37° C. for 23 hours. The reaction solution was cooled to room temperature and then diluted with ethanol (12 mL), to which diisopropyl ether (48 mL) was dropwise added under stirring. After 30 minutes of stirring, the precipitated deposit was collected by filtration and washed with a diisopropyl ether-ethanol mixed solvent (4:1). The resultant product was dissolved in 10% aqueous acetonitrile (16 mL), which was then dialyzed with distilled water (2 L×3) using a dialysis membrane (molecular cutoff of 12,000 to 14,000). The dialyzed solution was subjected to freeze-drying to provide the title compound (334 mg).

After hydrolyzing the compound in the same way as that in Example 1, the released gemcitabine was quantitated by high performance liquid chromatography (HPLC) under the same conditions as those in Example 1 to determine the gemcitabine content of the compound of the present invention. As a result, the content was 20.5% (w/w) (49.9% based on the carboxyl groups of the polycarboxylic acid) in terms of gemcitabine hydrochloride. In addition, when the compound was subjected to HPLC analysis, the content of free gemcitabine was 5.1%.

Example 5

Polymeric Derivative of Cytidine Antimetabolite of Formula (1) wherein R is Methyl Group; A is Acetyl Group; Average of n is 272; Average of m is 36; and X is Gemcitabine, Hydroxyl Group or L-Valine Benzyl Ester Residue N,N-Dimethylformamide (10.3 mL) and N,N-diisopropylethylamine (77.9 µL) were added to the compound (515 mg) described in Reference Example 11 and gemcitabine hydrochloride (134 mg), which was then stirred at 40° C. After dissolution, 2-ethoxy-1-ethoxycarbonyl-1,2-dihydroquinoline (EEDQ, 166 mg) was added thereto, which was stirred at 40° C. for 20 hours. The reaction solution was cooled to room temperature and then diluted with ethanol (20.6 mL), to which diisopropyl ether (82.4 mL) was dropwise added under stirring. The precipitated deposit was collected by filtration and washed with a diisopropyl ether-ethanol mixed solvent (4:1). The resultant product was dissolved in 30% aqueous acetonitrile (20 mL), which was then dialyzed with distilled water (2 L×3) using a dialysis membrane (molecular cutoff of 12,000 to 14,000). The dialyzed solution was subjected to freeze-drying to provide the title compound (574 mg).

After hydrolyzing the compound in the same way as that in Example 1, the released gemcitabine was quantitated by high performance liquid chromatography (HPLC) under the same conditions as those in Example 1 to determine the gemcitabine content of the compound of the present invention. As a result, the content was 14.1% (w/w) (28.8% based on the carboxyl groups of the polycarboxylic acid) in terms of gemcitabine hydrochloride. In addition, when the compound was subjected to HPLC analysis, the content of free gemcitabine was 0.2% or less.

Example 6

Polymeric Derivative of Cytidine Antimetabolite of Formula (1) wherein R is Methyl Group; A is Acetyl Group; Average of n is 272; Average of m is 26; and X is Gemcitabine, Hydroxyl Group or L-Phenylalanine Benzyl Ester Residue N,N-Dimethylformamide (75 mL) and N,N-diisopropylethylamine (286 µL) were added to the compound (3.0 g) described in Reference Example 12 and gemcitabine hydrochloride (492 mg), which was then stirred at 40° C. After dissolution, 2-ethoxy-1-ethoxycarbonyl-1,2-dihydroquinoline (EEDQ, 508 mg) was added thereto, which was stirred at 40° C. for 24 hours. The reaction solution was cooled to room temperature and then dropwise added to a diisopropyl ether-ethanol mixed solvent (4:1) (750 mL). After 30 minutes of stirring, the precipitated deposit was collected by filtration and washed with a diisopropyl ether-ethanol mixed solvent (4:1). The resultant product was dissolved in 50% aqueous acetonitrile (50 mL), which was then dialyzed with distilled water (3 L×3) using a dialysis membrane (molecular cutoff of 12,000 to 14,000). The dialyzed solution was subjected to freeze-drying to provide the title compound (2.94 g).

After hydrolyzing the compound in the same way as that in Example 1, the released gemcitabine was quantitated by high performance liquid chromatography (HPLC) under the same conditions as those in Example 1 to determine the gemcitabine content of the compound. As a result, the content was 4.67% (w/w) (11.9% based on the carboxyl groups of the polycarboxylic acid) in terms of gemcitabine hydrochloride. In addition, when the compound of the present invention was subjected to HPLC analysis, the content of free gemcitabine was 0.2% or less.

Example 7

Polymeric Derivative of Cytidine Antimetabolite of Formula (1) wherein R is Methyl Group; A is Acetyl Group; Average of n is 272; Average of m is 26; and X is Gemcitabine, Hydroxyl Group or 4-Phenylbutyl Alcohol Residue N,N-Dimethylformamide (50 mL) and N,N-diisopropylethylamine (218 µL) were added to the compound (2.07 g) described in Reference Example 14 and gemcitabine hydrochloride (375 mg), which was then stirred at 40° C. After dissolution, 2-ethoxy-1-ethoxycarbonyl-1,2-dihydroquinoline (EEDQ, 386 mg) was added thereto, which was stirred at 40° C. for 24 hours. The reaction solution was cooled to room temperature and then dropwise added to a diisopropyl ether-ethanol mixed solvent (4:1, 750 mL). After one hour of stirring, the precipitated deposit was collected by filtration and washed with a diisopropyl ether-ethanol mixed solvent (4:1). The resultant product was dissolved in 50% aqueous acetonitrile (25 mL), which was then dialyzed with distilled water (3 L×3) using a dialysis membrane (molecular cutoff of 12,000 to 14,000). The dialyzed solution was subjected to freeze-drying to provide the title compound (2.05 g).

After hydrolyzing the compound in the same way as that in Example 1, the released gemcitabine was quantitated by high performance liquid chromatography (HPLC) under the same conditions as those in Example 1 to determine the gemcitabine content of the compound of the present invention. As a result, the content was 7.35% (w/w) (17.5% based on the carboxyl groups of the polycarboxylic acid) in terms of gemcitabine hydrochloride. In addition, when the compound was subjected to HPLC analysis, the content of free gemcitabine was 0.2% or less.

Example 8

Polymeric Derivative of Cytidine Antimetabolite of Formula (1) wherein R is Methyl Group; A is Acetyl Group; Average of n is 272; Average of m is 32; and X is Cytarabine or Hydroxyl Group The N-acetylated block copolymer of a monomethoxy-polyethylene glycol having a molecular weight of about 12,000 with a polyglutamic acid having a polymerization number of about 32 (130 mg) described in Reference Example 4 and cytarabine (50.0 mg) were dissolved in N,N-dimethylformamide (2.6 mL), to which 2-ethoxy-1-ethoxycarbonyl-1,2-dihydroquinoline (EEDQ, 63.6 mg) was then added, followed by stirring at 40° C. for 24 hours. The reaction solution was cooled to room temperature and then diluted with ethanol (5.2 mL), to which diisopropyl ether (20.8 mL) was then dropwise added under stirring. After 30 minutes of stirring, the precipitated deposit was collected by filtration and washed with a diisopropyl ether-ethanol mixed solvent (4:1). The resultant product was dissolved in 20% aqueous acetonitrile, which was then dialyzed with distilled water (2 L×3) using a dialysis membrane (molecular cutoff of 12,000 to 14,000). The dialyzed solution was subjected to freeze-drying to provide the title compound (143 mg).

After hydrolyzing the compound, the released cytarabine was quantitated by high performance liquid chromatography (HPLC) to determine the cytarabine content of the compound. As a result, the content was 22.5% (w/w) (59.2% based on the carboxyl groups of the polycarboxylic acid) in terms of cytarabine.

Method of Hydrolysis

The title compound (3.20 mg) was dissolved in methanol (0.5 mL), to which concentrated ammonia water (0.5 mL) was then added before sealing, followed by stirring at 37° C. for one hour. The solution was neutralized with acetic acid and then diluted with distilled water to make an exact 10 mL of solution.

Analysis Conditions of HPLC (Analysis of Cytarabine)
Column: SUPELCO Discovery HS F5 (particle size: 5 μm), 4.6φ×250 mm;
Column temperature: 40° C.;
Eluent: phosphate buffer (10 mM, pH 6.9);
Flow rate: 1 mL/min.;
Detector (detection wavelength): UV (275 nm)

Example 9

Polymeric Derivative of Cytidine Antimetabolite of Formula (1) wherein R is Methyl Group; A is Acetyl Group; Average of n is 272; Average of m is 32; and X is Cytarabine, Hydroxyl Group or L-Phenylalanine Benzyl Ester Residue The compound (267 mg) described in Reference Example 10 and cytarabine (50.0 mg) were dissolved in N,N-dimethylformamide (5.3 mL), to which 2-ethoxy-1-ethoxycarbonyl-1,2-dihydroquinoline (EEDQ, 63.6 mg) was then added, followed by stirring at 40° C. for 21 hours. The reaction solution was cooled to room temperature and then diluted with ethanol (10.6 mL), to which diisopropyl ether (42.4 mL) was then dropwise added under stirring. After 30 minutes of stirring, the precipitated deposit was collected by filtration and washed with a diisopropyl ether-ethanol mixed solvent (4:1). The resultant product was dissolved in 30% aqueous acetonitrile, which was then dialyzed with distilled water (2 L×3) using a dialysis membrane (molecular cutoff of 12,000 to 14,000). The dialyzed solution was subjected to freeze-drying to provide the title compound (290 mg).

After hydrolyzing the compound in the same way as that in Example 8, the released cytarabine was quantitated by high performance liquid chromatography (HPLC) under the same conditions as those in Example 8 to determine the cytarabine content of the compound. As a result, the content was 11.3% (w/w) (31.5% based on the carboxyl groups of the polycarboxylic acid) in terms of cytarabine.

Test Example 1

Agent Release Test in the Absence of Enzyme

The compound of Example 1 (indicated with compound 1 in FIG. 1), the compound of Example 2 (indicated with compound 2 in FIG. 1), or the compound of Example 7 (indicated with compound 7 in FIG. 1) was dissolved in phosphate buffered saline (pH 7.4) so as to provide a concentration of 1.0 mg/mL, which was then allowed to stand at a constant temperature of 37° C. The amount of released gemcitabine was measured with time by HPLC to determine the percentage of the amount of released gemcitabine based on the amount of the total gemcitabine in the compound used. The results are shown in FIG. 1. As a result, the compounds of the present invention were demonstrated to slowly release the agents without depending on enzyme.

Test Example 2

Agent Release Test in Mouse Plasma

The compound of Example 1 (2.3 mg; indicated with compound 1 in FIG. 2) or the compound of Example 2 (3.7 mg; indicated with compound 2 in FIG. 2) was dissolved in phosphate buffered saline (0.1 mL, pH 7.4), to which a 4-fold amount (v/v) of the plasma (0.4 mL) collected and prepared from mice was then added, followed by allowing the mixture to stand at a constant temperature of 37° C. Fifty microliters each of aliquots were taken with time and diluted with 50% aqueous methanol (450 μL). The solution was subjected to deproteinization treatment using a membrane filter (pore size: 0.45 μm), followed by measuring the amount of released gemcitabine by HPLC to determine the percentage of the amount of released gemcitabine based on the amount of the total gemcitabine in the compound used. The results are shown in FIG. 2. The compounds of the present invention were demonstrated to slowly release the agents also in plasma.

Test Example 3

Antitumor Effect on Cancer-Bearing Mice (1)

Murine colon carcinoma Colon 26 was maintained by serial subcutaneous implantation in mice. The Colon 26 tumor was minced into about 2-mm square fragments and these tumor pieces were implanted to mice subcutaneously by trocar. Seven days after tumor implantation, the compound of Example 1 (indicated with compound 1 in Table 2), the compound of Example 2 (indicated with compound 2 in Table 2), the compound of Example 4 (indicated with compound 4 in Table 2), and gemcitabine hydrochloride as a control agent were dissolved in 5% glucose injection, respectively, and each compound or control agent was administered once intravenously at the doses described in Table 2. Tumor size was measured on the day starting administration and on day 7 following initiation of drug administration, and tumor volumes were calculated by using the following equation. Relative tumor volumes at 7 days after administration versus at the starting day were estimated. The results are shown in Table 2.

TABLE 2

[Equation 1]
$$\text{Tumor volume (mm}^3\text{)} = \frac{[\text{Major diameter of tumor (mm)}] \times [\text{Minor diameter of tumor (mm)}] \times [\text{Minor diameter of tumor}]}{2}$$

| Agent | Dose (in gemcitabine hydrochloride)(mg/kg) | Relative tumor Volume* |
|---|---|---|
| Non-treatment | 0 | 8.8 ± 4.9 |
| Compound 1 | 50 | 0.4 ± 0.2 |
|  | 25 | 1.5 ± 0.5 |

TABLE 2-continued $$\text{Tumor volume (mm}^3\text{)} = \frac{[\text{Major diameter of tumor (mm)}] \times [\text{Minor diameter of tumor (mm)}] \times [\text{Minor diameter of tumor}]}{2} \quad \text{[Equation 1]}$$

| Agent | Dose (in gemcitabine hydrochloride)(mg/kg) | Relative tumor Volume* |
|---|---|---|
| Compound 2 | 12.5 | 0.5 ± 0.3 |
|  | 6.25 | 2.4 ± 1.1 |
| Compound 4 | 25 | 0.5 ± 0.1 |
|  | 6.25 | 3.6 ± 0.5 |
| Control Agent | 200 | 1.4 ± 0.1 |
|  | 100 | 2.6 ± 0.7 |

*The mean relative tumor volume (mean ± SD) at 7 days after the start of administration when the tumor volume at the starting date of administration is set to 1.0.

It is apparent from these results that the compounds of the present invention have equivalent or higher antitumor effects at lower doses than gemcitabine hydrochloride as a control agent. It was also shown that the compound of the present invention having the hydrophobic substituent (the compound of Example 2 or 4) had a comparable effect at further reduced doses compared to the compound having no hydrophobic substituent (the compound of Example 1).

Test Example 4

Antitumor Effect on Cancer-Bearing Mice (2)

Murine colon carcinoma Colon 26 was maintained by serial subcutaneous implantation in mice. The Colon 26 tumor was minced into about 2-mm square fragments and these tumor pieces were implanted to mice subcutaneously by trocar. Seven days after tumor implantation, the compound of Example 7 (indicated with compound 7 in Table 3) and gemcitabine as a control agent were dissolved in 5% glucose injection, respectively, and each was administered once intravenously at the doses described in Table 3. Tumor volumes were calculated on the day starting administration and on day 10 following initiation of drug administration as described in Test Example 3. Relative tumor volumes at 10 days after administration versus at the starting day were estimated. The results are shown in Table 3.

TABLE 3

| Agent | Dose (in gemcitabine hydrochloride) (mg/kg) | Relative Tumor Volume* |
|---|---|---|
| Non-treatment | 0 | 10.5 ± 5.0 |
| Compound 7 | 25 | 0.3 ± 0.3 |
|  | 16.7 | 1.1 ± 0.5 |
| Control Agent | 200 | 3.4 ± 0.6 |
|  | 100 | 3.9 ± 0.5 |

*The mean relative tumor volume (mean ± SD) at 7 days after the start of administration when the tumor volume at the starting date of administration is set to 1.0.

It is apparent from these results that the compound of the present invention has an equivalent or higher antitumor effect at lower doses than gemcitabine hydrochloride as a control agent.

Test Example 5

Antitumor Effect on Cancer-Bearing Mice (3)

Murine colon carcinoma Colon 26 was maintained by serial subcutaneous implantation in mice. The Colon 26 tumor was minced into about 2-mm square fragments and these tumor pieces were implanted to mice subcutaneously by trocar. Seven days after tumor implantation, the compound of Example 8 (indicated with compound 8 in Table 4), the compound of Example 9 (indicated with compound 9 in Table 4), and cytarabine as a control agent were dissolved in 5% glucose injection, respectively, and each compound or control agent was administered once intravenously at the doses described in Table 4. Tumor volumes were calculated on the day starting administration and on day 10 following initiation of drug administration as described in Test Example 3. Relative tumor volumes at 10 days after administration versus at the starting day were estimated. The results are shown in Table 4.

TABLE 4

| Agent | Dose (in cytarabine) (mg/kg) | Relative Tumor Volume* |
|---|---|---|
| Non-treatment | 0 | 10.4 ± 4.0 |
| Compound 8 | 200 | 6.9 ± 1.3 |
|  | 100 | 9.4 ± 2.8 |
| Compound 9 | 150 | 5.7 ± 1.5 |
|  | 100 | 6.4 ± 0.5 |
| Control Agent | 1600 | 8.4 ± 2.9 |
|  | 800 | 10.0 ± 3.3 |
|  | 100 × 5** | 9.0 ± 2.0 |

*The mean relative tumor volume (mean ± SD) at 10 days after the start of administration when the tumor volume at the starting date of administration is set to 1.0.
**Five-day continuous administration at 100 mg/kg It is apparent from these results that the compounds of the present invention have higher antitumor effects at lower doses than cytarabine as a control agent. It was also shown that the compound having the hydrophobic substituent (the compound of Example 9) had a comparable effect at further reduced doses compared to the compound having no hydrophobic substituent (the compound of Example 8).

The invention claimed is:

1. A polymeric derivative of a cytidine antimetabolite, comprising a structure in which an amino group of a cytidine antimetabolite is amide-bonded to a carboxyl group in a side chain of a polymeric compound composed of a polyethylene glycol moiety and a polyglutamic acid chain moiety, wherein the derivative is a compound represented by general formula (1):

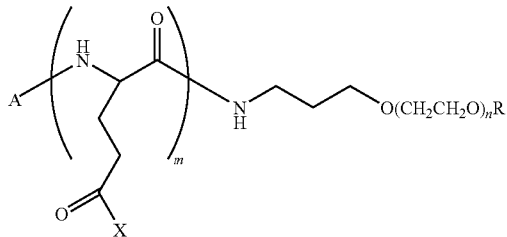

(1)

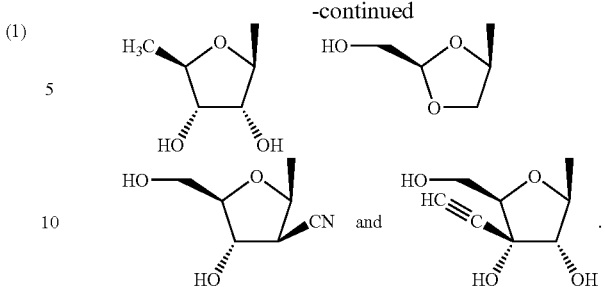

wherein R represents a hydrogen atom or a C1 to C6 alkyl group; A represents a hydrogen atom, a C1 to C6 acyl group, or a C1 to C6 alkoxycarbonyl group; m represents 3 to 200 as a mean value; n represents 5 to 2,000 as a mean value; X represents a cytidine antimetabolite residue, a hydroxyl group, or a hydrophobic substituent, wherein the proportion of the cytidine antimetabolite residue in X is 3 to 100% of m, the proportion of the hydroxyl group in X is 0 to 95% of m and the proportion of the hydrophobic substituent in X is 0 to 80% of m.

2. The polymeric derivative of a cytidine antimetabolite according to claim 1, wherein R represents a C1 to C3 alkyl group; A represents a C2 to C4 acyl group; m represents 5 to 100 as a mean value; n represents 50 to 1,000 as a mean value; and the cytidine antimetabolite residue represents a group represented by formula (2):

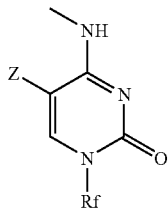

(2)

wherein Z represents a hydrogen atom or a fluorine atom; —Rf represents a group selected from the group consisting of substituents of formula (3)

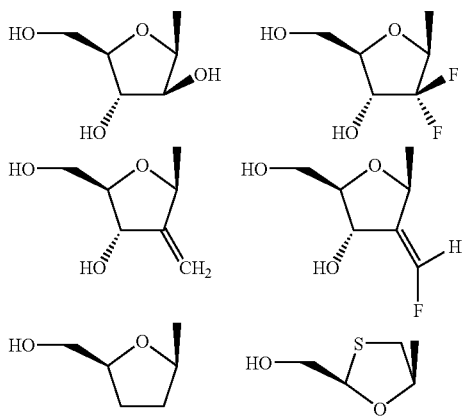

(3)

3. The polymeric derivative of a cytidine antimetabolite according to claim 1, wherein R represents a methyl group; A represents an acetyl group; m represents 10 to 60 as a mean value; n represents 100 to 300 as a mean value; X represents a cytidine antimetabolite residue or a hydroxyl group; and the cytidine antimetabolite represents cytarabine, gemcitabine, or 5'-deoxy-5-fluorocytidine.

4. The polymeric derivative of a cytidine antimetabolite according to claim 1 or 2, wherein the hydrophobic substituent represents an α-amino acid derivative represented by formula (4)

(4)

wherein Q represents a side chain of a neutral amino acid; W represents a C1 to C6 alkyl group or a benzyl group.

5. The polymeric derivative of a cytidine antimetabolite according to claim 4, wherein Q represents an isopropyl group or a benzyl group; and W represents a benzyl group.

6. The polymeric derivative of a cytidine antimetabolite according to claim 1 or 2, wherein the hydrophobic substituent represents a group represented by formula (5)

O-T  (5)

wherein T represents a C1 to C6 alkyl group optionally substituted by a phenyl group.

7. The polymeric derivative of a cytidine antimetabolite according to claim 6, wherein T represents a benzyl group, a 3-phenylpropyl group, a 4-phenylbutyl group, or a 5-phenylpentyl group.

8. The polymeric derivative of a cytidine antimetabolite according to claim 1, wherein R represents a methyl group; A represents an acetyl group; m represents 10 to 60 as a mean value; n represents 100 to 300 as a mean value; the cytidine antimetabolite represents cytarabine, gemcitabine, or 5'-deoxy-5-fluorocytidine; and the hydrophobic substituent represents a benzyloxy group, a 4-phenylbutoxy group, a (1-benzyloxycarbonyl-2-methyl)propylamino group, or a (1-benzyloxycarbonyl-2-phenyl)ethylamino group.

9. An antitumor agent comprising the polymeric derivative of a cytidine antimetabolite according to any one of claims 1 and 2 to 8 as a medicinal ingredient.

10. An antiviral agent comprising the polymeric derivative of a cytidine antimetabolite according to any one of claims 1 and 2 to 8 as a medicinal ingredient.

* * * * *